United States Patent [19]

Welch et al.

[11] 4,115,422

[45] Sep. 19, 1978

[54] ANTIBACTERIAL TEXTILE FINISHES UTILIZING ZIRCONYL ACETATE COMPLEXES OF INORGANIC PEROXIDES

[75] Inventors: Clark M. Welch, Metairie; Gary F. Danna, New Orleans, both of La.; Tyrone L. Vigo, Knoxville, Tenn.

[73] Assignee: The United States of America as represented by the Secretary of Agriculture, Washington, D.C.

[21] Appl. No.: 787,177

[22] Filed: Apr. 12, 1977

[51] Int. Cl.$^2$ .............................................. C07F 7/00
[52] U.S. Cl. ................. 260/429.3; 106/15 R; 252/8.6; 424/66; 428/907; 427/354; 427/394
[58] Field of Search ............ 106/15 R; 252/8.6; 428/907; 260/2M, 429.3; 424/66; 427/354, 394

[56] References Cited

U.S. PATENT DOCUMENTS

| | | | |
|---|---|---|---|
| 2,681,922 | 6/1954 | Balthis | 260/429.3 X |
| 2,956,071 | 10/1960 | Samour | 260/429.3 |
| 3,183,118 | 5/1965 | Conner | 260/429.3 X |
| 3,407,254 | 10/1968 | Siegal et al. | 424/66 |

*Primary Examiner*—Michael R. Lusignan
*Attorney, Agent, or Firm*—M. Howard Silverstein; David G. McConnell; Salvador J. Cangemi

[57] ABSTRACT

Bacteriostatic, water-insoluble complexes of zirconyl acetate with inorganic peroxides are disclosed. Peroxides operative in forming these complexes are hydrogen peroxide, alkali metal perborates and alkali metal peroxydiphosphates. Processes for in situ formation and deposition of the insoluble complexes on the surfaces of cellulosic textiles are described. The textile finishes so produced inhibit the growth and spreading of odor- and infection-producing gram-negative and gram-positive bacteria on the treated textiles. The antibacterial activity imparted to the textiles is durable to repeated laundering.

10 Claims, No Drawings

ANTIBACTERIAL TEXTILE FINISHES UTILIZING ZIRCONYL ACETATE COMPLEXES OF INORGANIC PEROXIDES

BACKGROUND OF THE INVENTION (1) Field of the Invention

This invention relates to a new method of imparting antibacterial activity to cellulosic textiles. More particularly, this invention relates to a new method of forming water-insoluble peroxide complexes of zirconyl acetate as deposits, films, and coatings on and within cellulosic fibers, yarns, and fabrics, as well as paper.

(2) Description of the Prior Art

While many types of antibacterial agents have previously been applied to cellulosic and non-cellulosic textiles, seldom have the products possessed a combination of strong activity against undesirable bacterial, together with high durability of antibacterial activity to repeated launderings. In many instances the antibacterial agents previously used have had undesired physiological side effects on contact with human skin or exposed tissue, or they adversely affected the color and feel of the textile, and in addition, were expensive to manufacture, as indicated by Gagliardi, *American Dyestuff Reporter*, P49-58 (Jan. 22, 1962).

The processes of the present invention utilize hydrogen peroxide and its inorganic derivatives as inexpensive reagents from which water-insoluble, colorless peroxide complexes of zirconyl acetate are formed on the cellulosic textile. It is hypothesized that the high moisture content of the cellulosic substrate interacts very gradually with the insoluble peroxide complexes of zirconyl acetate to give a slow but continual release of hydrogen peroxide and zirconyl ions from the fabric as the active antibacterial agents. Evidence for this hypothesis lies in the finding that although the peroxide complexes of zirconyl acetate can just as readily be formed on 100% polyester textiles as on cellulosic textiles, the treated polyester textiles are found to possess only slight antibacterial activity even at high measured peroxide contents. Since polyester textiles contain only small amounts of moisture, of the order of 5%–10% of that in cellulosic textiles at ordinary humidities, it appears that the available moisture content of the textile material is highly critical to the antibacterial activity of the treated material, as would be expected if water were needed to generate hydrogen peroxide by reaction with the insoluble peroxide complexes of zirconyl acetate. In any event, the much greater effectiveness of the present antimicrobial treatment on cellulose than on polyester shows that the effectiveness of the present invention is neither obvious nor predictable from the known antiseptic properties of simple inorganic peroxides studied previously.

The methods of forming peroxide complexes of zirconyl acetate on solid cellulosic materials, as developed in this invention, are also novel. The prior art suggests no method whereby the complexes can be kept in solution prior to and during their application to cellulosic textiles, but subsequently can be insolubilized on the textile material, thus being rendered durable to washing or leaching. The high durability of the antimicrobial activity imparted is a major advantage of the present invention over the processes of the prior art. It is well known that certain insoluble peroxides of zirconium can be formed by adding an alkali metal hydroxide to a mixture of a soluble zirconium salt and hydrogen peroxide in aqueous solution. It is also known that at very high acidities, aqueous solutions of zirconium salts interact with hydrogen peroxide to yield soluble peroxide complexes of zirconium. Neither of these processes is suitable for the treatment of textiles, or suggests any means of depositing the complexes in insoluble form on cellulosic substrates. The prior art on zirconium peroxides is reviewed by Blumenthal, "The Chemical Behavior of Zirconium," D. Van Nostrand Co., 1958, pp 198-200. Rot resistant finishes for cotton based on phenolic complexes of zirconium acetate were reported by Gonzales et al, Textile Res. J. 33, 600-608 (1963).

It has been well known for many years that hydrogen peroxide by itself is a safe and effective topical and oral antiseptic and disinfectant, when used in dilute aqueous solutions, and it can be used to cleanse open wounds. The present invention offers for the first time a means of bonding complexes of hydrogen peroxide to cellulosic textile, thus affording a new means of application of this antibacterial agent. Likewise, alkali metal perborates are known antiseptics but the prior literature furnishes no method for durably bonding them to cellulose. The prior art also discloses no means of bonding alkali metal peroxydiphosphates to cellulosic substrates.

SUMMARY OF THE INVENTION

A process for imparting antibacterial activity to cellulosic textiles is disclosed in which the textile is treated with an aqueous solution containing 1%–35% by weight of zirconyl acetate, 0.3%–35% of acetic acid and 1%–25% of an inorganic peroxide, followed by heat drying of the textile to convert the water-soluble agents to insoluble peroxide complexes of zirconyl acetate. As the inorganic peroxides required for this one-bath treating process, hydrogen peroxide and alkali metal perborates were suitable and effective.

Optionally, the cellulosic textile was treated with a 1%–40% solution of zirconyl acetate in water, followed by heat drying of the textile, and was subsequently treated with a 1%–30% aqueous solution of an inorganic peroxide, followed by heat drying of the textile. Inorganic peroxides which were suitable for this two-bath treating process were hydrogen peroxide, alkali metal perborates, and alkali metal peroxydiphosphates.

These new treatments inhibit the growth and spreading of odor- and infection-producing bacteria on cellulosic textiles, and the antibacterial activity imparted to the textile is durable to repeated laundering.

The present invention also includes the preparation of water-insoluble peroxide complexes of zirconium acetate in the absence of a textile substrate, as a means of obtaining antibacterial dusting powders.

DESCRIPTION OF THE PREFERRED EMBODIMENTS

In the description that follows, all parts and percentages are by weight. The zirconyl acetate, a compound having the formula $ZrO(OOCCH_3)_2$, was available as a commercial aqueous solution containing 40% zirconyl acetate equivalent to a zirconium oxide ($ZrO_2$) content of 22%. This solution remained clear even when diluted with water in all proportions.

If, however, a 10%–30% aqueous solution of hydrogen peroxide were added at 10° C.–50° C. to a 1%–40% aqueous solution of the zirconyl acetate, to yield a mixture containing about 0.1–3.0 moles zirconyl acetate per mole of hydrogen peroxide, an insoluble gelatinous precipitate began to form and after 0.5 minutes to 30 minutes, the entire mixture set to a gel. Addition of excess hydrogen peroxide aided in driving the reaction to completion, the insoluble, crosslinked, hydrated, polymeric complex that was formed between zirconyl acetate and hydrogen peroxide is believed to have the structure

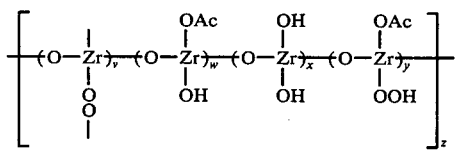

where the values of $v$, $w$, $x$, $y$, and $z$ vary with the reagent concentrations and the mole ratio of zirconyl acetate to hydrogen peroxide used in running the reaction. The filtered and dried solid produced in the reaction was found by chemical analysis to contain as much as 49.0% zirconium and 5.75% peroxide groups, as well as 17.6% acetyl groups, when the above mole ratio was 1:6. The use of lower proportions of hydrogen peroxide resulted in a lower peroxide content in the polymeric complex. The high acetyl content in the product proves that the complex is not a simple zirconium peroxide of the type $ZrO_3.2H_2O$ previously discussed by Blumenthal in the reference cited above.

It should be noted that the gel, once it forms, gradually undergoes further chemical reaction, and after standing 18-24 hours at room temperature, undergoes reliquefaction to give a clear solution. A 90% decrease in peroxide content occurs within a few hours on further standing, but the solution, if applied to fabric soon after the reliquefaction occurs, does impart a degree of antibacterial activity.

A further discovery is that the above gel formation, which occurs on mixing zirconyl acetate and hydrogen peroxide solutions, can be prevented by adding acetic acid to the zirconyl acetate solution prior to adding the hydrogen peroxide. A clear solution of zirconyl acetate, acetic acid and hydrogen peroxide can in this way be prepared. When this solution was applied to a cellulosic textile such as cotton fabric, subsequent heat drying of the impregnated fabric volatilized the acetic acid and water, whereupon water-insoluble complexes of zirconyl acetate with hydrogen peroxide were deposited on the fabric to impart a high degree of antibacterial activity. Since hydrogen peroxide is less expensive than zirconyl acetate, hydrogen peroxide was normally added in excess over the zirconium salt in this one-bath textile treatment. Under these conditions, the concentrations of acetic acid needed to prevent gellation of the treating bath was governed by the zirconyl acetate concentration used. The minimum effective ratio by weight of acetic acid to zirconyl acetate was about 0.3:1. When the proportion of acetic acid was appreciably less than this, the treating bath was liable to gel within a very short time. Higher proportions of acetic acid could readily be used, but above a weight of about 5:1 of acetic acid to zirconyl acetate, there was little further advantage to be gained in regard to bath stability and the irritating odor of acetic acid in the treating bath became pronounced.

In place of hydrogen peroxide in the one-bath textile treatment may be used an alkali metal perborate. Zirconyl acetate in 1%-40% aqueous solution readily reacted at 10° C.-50° C. with 1%-10% aqueous solutions of alkali metal perborates when the two agents were mixed together in mole ratios of 0.1-3.0 moles zirconium compound to each mole of perborate. A gelatinous precipitate of an insoluble perborate complex of zirconyl acetate quickly formed. The precipitation could be prevented by addition of acetic acid prior to addition of perborate. The amount of acetic acid required was the same as for hydrogen peroxide-zirconyl acetate mixtures. The most economical and readily available perborate is sodium perborate tetrahydrate, $NaBO_3.4H_2O$, sometimes referred to as sodium peroxyborate tetrahydrate. An alkali metal perborate monohydrate, $MBO_3.H_2O$, is also effective. By contrast, alkali metal persulfates, $M_2S_2O_8$, known also as alkali metal peroxydisulfates, did not form water-insoluble complexes with zirconium acetate, and when applied to cotton fabric with zirconium acetate and dried, the peroxydisulfates quickly leached out of the fabric during subsequent washing. Alkali metal peroxydisulfates are, therefore, inoperative in the processes of this invention.

Aqueous solutions of alkali metal peroxydiphosphates such as $K_4P_2O_8$ readily formed insoluble complexes with aqueous zirconyl acetate, when mixed at 10°-50° C. in a ratio of 0.1-3.0 moles of zirconyl acetate per mole of alkali metal peroxydiphosphate, at concentrations similar to those suitable for perborates. However, the precipitation of the complexes could not be prevented by adding acetic acid prior to adding the peroxydiphosphate. The alkali metal peroxydiphosphates are therefore inoperative in the one-bath textile finishing process, though they are effective in a two-bath process to be described later in this disclosure.

The operative mole ratios of zirconyl acetate to hydrogen peroxide or to alkali metal perborate in the one-bath textile treatment were in the range of about from 0.1:1 up to about 3:1. As already indicated, hydrogen peroxide and an alkali metal perborate tetrahydrate are less expensive than zirconyl acetate, and it is therefore advantageous to use the inorganic peroxides in excess over the zirconyl salt, in order to drive the desired complex formation rapidly to completion during the heat-drying of the textile.

The above findings have been used to develop the one-bath processes of this invention for the preparation of bacteriostatic textiles. The preferred process utilizes an acetic acid-stabilized bath and comprises the following steps:

(a) preparation of an aqueous treating solution containing about from 1% to 35% zirconyl acetate, 0.3% to 35% acetic acid, and 1% to 25% of an inorganic peroxide selected from the class consisting of hydrogen peroxide, an alkali metal perborate monohydrate and an alkali metal perborate tetrahydrate, the solution being made up by adding the inorganic peroxide to a solution of the zirconyl acetate and acetic acid in water, the ratio by weight of acetic acid to zirconyl acetate being from about 0.3:1 to about 5:1, and the mole ratio of zirconyl acetate to inorganic peroxide being from about 0.1:1 to about 3:1, (b) immersion of a cellulosic textile in the aqueous treating solution for a period of time sufficient to thoroughly wet the cellulosic textile, (c) removal of excess treating solution from the cellulosic textile, (d) heating the cellulosic textile at a temperature of from about 50° C. to 160° C. for about from 0.5 minutes to 30 minutes to dry the cellulosic textile and cause deposition of peroxide complexes of zirconium on the textile, the higher temperature being maintained for the shorter times, (e) washing the cellulosic textile to remove excess reagents, and (f) drying the treated cellulosic textile at a temperature of 50° C. to 140° C. for from 0.5 minutes to 30 minutes, the higher temperatures being used for the shorter times.

In the above one-bath textile finishing process, the treating bath prepared as in step (a) may contain the reagents in a wide range of concentrations, as indicated. In the case where the inorganic peroxide is an alkali metal perborate monohydrate or tetrahydrate, the upper limits of concentration are governed by the solubility of these agents in dilute aqueous acetic acid at the bath temperature used, which may be in the range 10° C.–50° C. Regardless of which of the inorganic peroxides specified in step (a) is used, the acetic acid must be added to the treating solution prior to addition of the peroxide, if gellation is to be prevented. Once gellation has occurred in the treating solution, it is very difficult to redissolve the gelatinous solids, and the treating solution is found to be much less effective in imparting antibacterial properties to cellulosic textiles. Thus the order of addition in preparing the textile treating solution is critical to the successful operation of the present invention.

In step (b), the cellulosic textile may be treated either in batches, or may be continuously passed through the treating solution at any speed which permits thorough and uniform wetting of the textile. If a wetting agent is to be used, it should be nonionic, in order that the precipitation of zirconyl or peroxide complexes in the treating bath may be avoided.

In step (c) the excess treating solution may be removed by various mechanical methods such as by passing the textile between squeeze rolls to wring excess liquid from the textile, or by centrifugation, or draining.

In step (d), the purpose of heat drying is not only to remove water and acetic acid by volatilization, so as to cause the zirconyl acetate to react rapidly and completely with the inorganic peroxide to form insoluble peroxide complexes of zirconyl acetate, but also to convert the resulting hydrated, gelatinous complexes into the smooth, non-sticky, dehydrated layers of insoluble complexes durably deposited on or within fibers, yarns, fabrics, and sheets of the cellulosic material. This heating step is critical to the process, in that too high a temperature can cause thermal decomposition of the peroxide complexes of zirconyl acetate, if maintained for too long a time. The higher the temperature used, the shorter is the time required. Too low a temperature for a given heating time results, on the other hand, in incomplete deposition of peroxide complexes of zirconium and produces a gelatinous, easily removable coating of the cellulosic textile. The heating step may be carried out in an oven, preferably one having a forced draft of air directed at the surface of the textile and exhausting through a vent to remove fumes of acetic acid and water vapor.

Washing of the treated textile, step (e), may be carried out with either hot or cold water, inasmuch as the peroxide complexes of zirconyl acetate on the fabric are stable and insoluble at ordinary washing temperatures, and are highly resistant to removal by agitation or rubbing such as occurs in clothes washing machines.

Final drying of the cellulosic textile, step (f), can be carried out by any ordinary means such as oven drying, line drying, or by tumble drying in a mechanical clothes drier. High temperatures in excess of 140° C. should be avoided to ensure against thermal decomposition of the peroxide complexes of zirconyl acetate in the textile material. A drying temperature of 80° C.–120° C. for 1–5 minutes is particularly preferred, although still higher temperatures can be used for shorter times.

Less preferably is the one-bath process in which acetic acid is not added as a bath stabilizer, but in which 10%–30% aqueous hydrogen peroxide solution is added to 1%–40% aqueous zirconyl acetate solution at 10° C.–50° C. to produce a gel, which is then stored at 10° C.–35° C. for 18–24 hours to allow the gel to reliquefy to give a treating solution, which is then applied to the textile and heat-cured as in the one-bath process just described.

As a further embodiment of the present invention, a two-bath textile treatment has been developed. The two-bath treatment has the advantage that since the zirconyl acetate and the inorganic peroxide are applied separately to the cellulosic textile, it is not necessary to add acetic acid as a bath stabilizer. Moreover, a wider range of inorganic peroxides can be used in the two-bath process, since the peroxide and the zirconyl acetate do not need to be mutually compatible in aqueous solution, in this case.

The two-bath process for the preparation of bacteriostatic textiles of this invention comprises the following steps:

(a) immersion of the cellulosic textile in an aqueous treating solution containing about from 1% to 40% of zirconyl acetate in water, (b) removal of excess treating solution from the cellulosic textile, (c) heating the cellulosic textile at about from 50° C. to about 160° C. for from 0.5 minute to 30 minutes to dry the cellulosic textile and to convert the soluble zirconyl acetate to an insoluble zirconium oxyacetate complex deposited on the cellulosic textile, the higher temperature being used for the shorter times, (d) immersion of the cellulosic textile in an aqueous treating solution containing about from 1% to 30% of an inorganic peroxide selected from the class consisting of hydrogen peroxide, an alkali metal perborate monohydrate, an alkali metal perborate tetrahydrate, and an alkali metal peroxydiphosphate, the immersion being contained for a time sufficient to thoroughly wet the textile, (e) removal of excess treating solution from the cellulosic textile, (f) heating the cellulosic textile at about from 50° C. to about 160° C. for from 0.5 minutes to 30 minutes, the higher temperatures being used for the shorter times, to dry the cellulosic textile and to produce an insoluble peroxide complex of the zirconium oxyacetate deposited on the cellulosic textile, (g) washing the cellulosic textile to remove excess reagents, and (h) drying the treated cellulosic textile at temperatures of 50° C.–140° C. for from 0.5 minute to 30 minutes, the higher temperatures being used for the shorter times.

Steps (a), (b), and (c) of the above two-bath textile finishing process are similar to the first three steps of the double pad method of Gonzales et al, *Textile Research J.* 33 600(1963), who showed that when aqueous zirconyl acetate is applied to cotton fabric and heat-cured, the zirconium salt undergoes olation, i.e., partial hydrolysis accompanied by condensation polymerization to an insoluble poly(zirconium oxyacetate) apparently having a ... ZrOZrOZr ... backbone and pendant acetate side groups readily replaceable by other anionic groups such as fatty acid anions or phenolate anions. The present invention departs from their process in that peroxide groups replace pendant acetate groups as a result of the present processes, thus producing novel, insoluble, polymeric peroxide complexes of zirconyl acetate on the cellulosic textile.

In step (d) of the 2-bath process of this invention, the upper limits of the usable concentrations of alkali metal perborate or peroxydiphosphate are governed solely by the solubility of these agents in water at the bath temperature used, which may be in the range 10° C.–50° C.

The same considerations apply to steps (e), (f), (g), and (h) of the two-bath process were discussed in connection with steps (c), (d), (e), and (f) of the one-bath process.

In the examples that follow, all parts and percentages are by weight. Analyses for zirconium, boron and acetyl content were performed by a commercial laboratory. Analyses for peroxide (—O—O—) groups in treated fabric were conducted iodometrically by a procedure similar to that of Wentz and Cates, *Textile Research J.*, 45, 691 (1975), as follows: 50 ml distilled water, 1 ml of 37% aqueous hydrochloric acid and 1 ml of saturated aqueous potassium iodide were added to the weighed fabric sample, and the mixture was heated on a steam cone for 10 min. followed by titration with standardized 0.1 N sodium thiosulfate. The peroxide content of isolated zirconium acetateinorgaic peroxide complexes was similarly determined except that sufficient hydrochloric acid was added prior to titration to bring all the complex into aqueous solution. Antibacterial activity of treated fabrics was determined qualitatively by the parallel streak test of the American Association of Textile Chemists and Colorists (AATCC Test Method 147-1976) with the gram-positive bacteria *Staphylococcus aureus* and the gram-negative bacteria *Klebsiella pneumoniae*. Quantitative tests for antibacterial activity were run by the Quinn method (AATCC Test Method 100-1974) using gram-positive *Staphylococcus epidermidis* bacteria. The first two of these species of bacteria are capable of causing infection, while the third acts on human perspiration to produce an undesirable odor often referred to as "body odor." Durability of the fabric finishes to laundering was determined in an agitator type washing machine and tumble dryer of the type specified in AATCC Test Method 124-1975, using normal conditions for cotton (14 minute hot water wash, 30minute high temperature drying) using the commercial AATCC standard detergent 124. The 80×80 cotton printcloth used weighed 3.2 oz. per square yard.

EXAMPLE 1

Preparation of a Water-Insoluble Complex of Zirconyl Acetate with Hydrogen Peroxide To 16.5 parts by weight of 20% aqueous zirconyl acetate, $ZrO(OOCCH_3)_2$, was added in small portions at 25° C., 20.4 parts of 15% aqueous hydrogen peroxide with stirring in a beaker. The mole ratio of zirconyl acetate to hydrogen peroxide was 0.16:1.00. Gellation of the reaction mixture occurred during the addition of the hydrogen peroxide. After peroxide addition was complete, the slurry was filtered by suction, and the gelatinous solid was dried at 80°C. for 1½ hours. This solid was further dried at 80° C. under vacuum at 3 mm. pressure for 6 hours whereupon the solid came to constant weight. The product had the following analysis: 49.0% zirconium, 5.75% peroxide groups and 17.6% acetyl groups.

In a second preparation, 0.93 parts by weight of 30% aqueous hydrogen peroxide was added with stirring to 4.6 parts of 40% aqueous zirconyl acetate at 23° C. The mole ratio of the two reagents was 1:1. Within 2 minutes the mixture had gelled to a sticky semi-solid product. After 30 minutes the product had hardened to a pulverizable solid. The solid was stirred in 50 parts of water for 5 minutes to extract any unreacted zirconyl acetate and hydrogen peroxide, and then was filtered by suction. The solid was washed with 10 parts of water and again filtered by suction. The solid was dried for 3 hours at 25° C. at reduced pressure (3 mm), the drying being interrupted every 45 minutes in order to triturate the solid to a more finely divided powder. At the end of this 3 hour drying period, the solid came to constant weight. The yield of product was 1.30 parts by weight of a white solid having a peroxide group content of 2.9%, and a zirconium content of 46.5%. The acetyl content was 3.62%.

The results show that in the absence of added acetic acid, the mixing of aqueous hydrogen peroxide with aqueous zirconyl acetate yields a water-insoluble complex. The ratio of zirconium atoms to peroxide groups in the complex varies with the mole ratio of zirconyl acetate to hydrogen peroxide used in preparing the complex.

EXAMPLE 2

One-Bath Textile Finishing Process with Zirconyl Acetate-Hydrogen Peroxide Complex at High Reagent Concentrations To 23.5 parts by weight of water in a beaker was added 42.5 parts of 40% aqueous zirconyl acetate and 8.0 parts glacial acetic acid, with thorough mixing at 25° C. Then 26.0 parts of 30% aqueous hydrogen peroxide were added, to give a clear solution containing 17% zirconyl acetate, 8% acetic acid and 7.8% hydrogen peroxide. Desized, scoured and bleached 80×80 cotton printcloth was immersed in the freshly prepared solution for one minute, and then was passed between squeeze rolls adjust to give a wet pickup of 117%. The fabric was heat cured in a forced-draft oven for 5 minutes at 80° C. It was then washed 30 minutes in hot (60° C.) running water and dried for 5 minutes at 80° C.

The fabric weight gain was 16.3%, and zirconium content of the fabric was 4.2%. The fabric contained 0.33% peroxide groups. In the parallel streak test with *Staph. aureus* and *K. pneumoniae*, the fabric showed no undergrowth of bacteria, in contrast to untreated fabric which had extensive undergrowth.

If the above treatment were carried out with a 5-minute cure at 160° C., the resulting fabric contained only 0.18% peroxide oxygen, and the parallel streak test produced a small amount of bacterial undergrowth The results show that the presence of acetic acid in the treating bath prevents precipitation of the insoluble complex of zirconium acetate with hydrogen peroxide, such as occurred in Example 1, and thus permits the treating solution to be applied to the textile. The result also show that the textile treatment imparts antibacterial activity. The most effective treatment was at the lower curing temperature (80° C.). A cure at 160° C. thermally decomposed some of the peroxide complex which had been formed on the fabric.

EXAMPLE 3

One-Bath Textile Finishing Process with Zirconyl Acetate-Hydrogen Peroxide Complex at Medium Concentrations of Reagents To 55.3 parts by weight of water in a beaker was added 24.8 parts of 40% aqueous zirconyl acetate and 4.6 parts of glacial acetic acid with thorough mixing at 25° C. Then 15.3 parts of 30% aqueous hydrogen peroxide was added, to give a clear solution containing 9.9% zirconyl acetate, 4.6% acetic acid and 4.6% hydrogen peroxide. Desized, scoured and bleached 80×80 cotton printcloth was immersed in the freshly prepared solution for one minute, and was then passed between squeeze rolls adjusted to give a 115% wet pickup. The fabric was heat cured in a forced-draft oven for 5 minutes at 80° C. It was then washed 30 minutes in hot (60° C.) running water and dried for 5 minutes at 80° C.

The fabric weight gain was 10.0% and the zirconium content of the fabric was 2.9%. The fabric contained 0.27% peroxide groups. In the parallel streak test with *Staph. aureus* and *K. pneumoniae* bacteria, the fabric showed no undergrowth of bacteria, in contrast to untreated fabric which had extensive undergrowth. Also the fabric was subjected to the Quinn test with the odor-causing bacteria *Staph. epidermidis*, and gave a 100% reduction in the number of bacterial colonies observed with untreated fabric.

After being subjected to 20 launderings and tumble dryings in a standard washing machine and dryer, using AATCC standard detergent 124, the treated fabric still contained 2.3% zirconium, and 0.05% peroxide groups. It showed no bacterial undergrowth in the parallel streak test with *Staph. aureus* and *K. pneumoniae* whereas untreated fabric had extensive undergrowth. In the Quinn test run as above, it produced a 98% reduction in the number of bacterial colonies observed with untreated fabric.

The data show that when zirconyl acetate-hydrogen peroxide complex is formed and deposited in situ on a cellulosic textile, this bacteriostatic complex is highly resistant to removal by repeated laundering.

EXAMPLE 4

One-Bath Finishing of Cotton-Nylon Blend Fabric

The textile finishing treatment of Example 3 was applied to a desized, scoured and bleached (43×43 fabric which was made of 70% cotton-30% nylon fiber blend and weighed 4.3 oz per sq yard. The treated fabric had a weight gain of 8.1% and contained 3.5% zirconium and 0.20% peroxide groups by chemical analysis. The treated fabric showed no bacterial undergrowth in the parallel streak test, whereas the untreated fabric showed extensive undergrowth of *Staph. aureus* and *K. pneumoniae*. In the Quinn test, treated fabric gave a 70% decrease in number of bacterial colonies relative to untreated fabric, using *Staph. epidermidis* bacteria.

The results show that the blending of cotton with nylon decreases somewhat the effectiveness of the antibacterial treatment, when measured by the Quinn test with *Staph. epidermidis*, but did not impair the effectiveness of the fabric finish in inhibiting *Staph. aureus* or *K. pneumoniae* in the parallel streak test.

EXAMPLE 5

Attempted One-Bath Finishing of Polyester Fabric

A commercial polyester sheeting was given the textile finishing treatment of Example 3. The treated fabric had a weight gain of 9.8%, and contained 2.0% zirconium, as well as 0.27% peroxide groups, as determined by chemical analysis. In the Quinn test run on this treated cloth with *Staph. epidermidis* bacteria, the reduction in number of bacterial colonies was only 22% relative to untreated fabric, which was completely inactive against the bacteria.

The results show that although the polyester sheeting had been treated to the same level of peroxide content as the cotton fabric in Example 3, the finish on the polyester sheeting was relatively ineffective in inhibiting bacterial growth. This demonstrates the unexpected specificity of the antibacterial action of the textile finishes of this invention, which finishes are operative chiefly on cellulosic textiles and blends thereof.

EXAMPLE 6

One-Bath Finish Omitting Acetic Acid as the Bath Stabilizer

To 1.17 parts by weight of 40% aqueous zirconyl acetate at 22° C. in a beaker was added 1.00 part by weight of 30% aqueous hydrogen peroxide. Gellation of the mixture occurred immediately, and over a period of 19 minutes, the temperature of the mixture rose spontaneously to 83° C. Some fumes and vapors were evolved which were presumed to be water vapors and oxygen. The gelled mixture was allowed to cool over a period of 2½ hours to room temperature, and after 22 hours further at 24° C., it reliquefied to give a clear solution.

Desized, scoured and bleached 80×80 cotton printcloth was immersed in this solution, was passed between squeeze rolls, was again immersed in the solution and again passed between squeeze rolls adjusted to give a wet pickup of 96%. The fabric was then oven-cured at 85° C. for 5 minutes. It was washed in hot running water for 30 minutes and was oven-dried at 85° C. for 5 minutes. The treated fabric had a weight gain of 17.7%, a peroxide content of 0.41%, and a zirconium content of 5.9%.

In the Quinn test with *Staph. epidermidis* bacteria, the treated fabric initially showed no decrease in bacteria count relative to the untreated control fabric. After 20 laundering cycles, however, some antibacterial activity was evident, there being 63% fewer bacteria on the treated cloth than on the untreated cloth. The decrease was 46% after 35 launderings and 16% after 50 launderings.

In the parallel streak test with *Staph. aureus* and *K. pneumoniae* bacteria, very slight bacterial undergrowth was observed at 0, 5, 20, 35, and 50 laundering cycles, whereas the untreated fabric showed extensive bacterial undergrowth.

The results show that in the absence of acetic acid to prevent bath gellation, the gel eventually reliquefied but the resulting solution was less effective in antibacterial finishing of textiles than treating solutions which contained the acetic acid.

EXAMPLE 7

Two-Bath Textile Finishing Process with Zirconyl Acetate and Hydrogen Peroxide

Desized, scoured and bleached 80×80 cotton printcloth was immersed in a 20% aqueous solution of zirconyl acetate for one minute, and was passed between squeeze rolls adjusted to give a wet pickup of 90%. The cloth was then heat cured for 5 minutes at 135° C. Subsequently it was immersed in an 18% aqueous solution of hydrogen peroxide and passed between squeeze rolls adjusted to give a wet pickup of 54%. The cloth was then heat-cured for 5 minutes at 85° C., followed by washing of the fabric for 30 minutes in hot (60° C.) running water. The cloth was dried at 85° C. for 5 minutes. The treated fabric had a weight gain of 12.6%, and contained 4.0% zirconium as well as 0.42% peroxide groups. The treated fabric showed no bacterial undergrowth in the parallel streak test with *Staph. aureus* and *K. pneumoniae* bacteria. Untreated fabric had extensive undergrowth when subjected to this test.

The results show that the hydrogen peroxide underwent complexation with zirconyl acetate already deposited on the fabric as a polymeric zirconium oxyacetate and the hydrogen peroxide was bound to the fabric, thereupon imparting to the fabric a high degree of antibacterial activity.

EXAMPLE 8

Preparation of a Water-Insoluble Complex of Zirconyl-Acetate with Sodium Perborate Tetrahydrate To 30 parts by weight of distilled water was added 1.25 parts of sodium perborate tetrahydrate, $NaBO_3 \cdot 4H_2O$. The mixture was warmed to 45° C. whereupon the sodium perborate tetrahydrate went into solution. Then 2.3 parts of 40% aqueous zirconyl acetate (0.5 mole per mole of perborate) was added to the solution, resulting in immediate precipitation of a gelatinous solid. The mixture was stirred, cooled to 30° C., and filtered by suction. The solid was washed with 150 parts of distilled water. It was then dried to constant weight at 24° C. under partial vacuum at 3 mm pressure for 3 hours, the vacuum being released once every 30 minutes so that the solid could be stirred and triturated to a more finely divided powder. The yield of cream-colored solid was 0.84 part by weight.

The product contained 9.34% peroxide groups by iodometric titration. The zirconium content was 33.9% and the boron content was 9.9%. The acetyl content was 0.63%.

EXAMPLE 9

One-Bath Textile Finishing Process with Zirconyl Acetate-Sodium Perborate Complex To 59.7 parts by weight of water in a beaker was added 25.3 parts of 40% aqueous zirconyl acetate and 5.0 parts of glacial acetic acid, with thorough mixing at 25° C. Then 10.0 parts of sodium perborate tetrahydrate were added, to give a clear solution containing 10.1% zirconyl acetate, 5.0% acetic acid and 10.0% sodium perborate tetrahydrate. Desized, scoured and bleached 80×80 cotton printcloth was immersed in the freshly prepared solution for one minute, and then was passed between squeeze rolls adjusted to give a wet pickup of 88%. The fabric was heat cured in a forced-draft oven for 5 minutes at 85° C. It was then washed 30 minutes in hot (60° C.) running water and dried for 5 minutes at 85° C.

The fabric weight gain was 7.1% and the zirconium content of the fabric was 3.1%, the boron content was 0.1% and the peroxide group content was 0.41%. The treated fabric exhibited very slight bacterial undergrowth in the parallel streak test with *Staph. aureus* and *K. pneumoniae*, whereas untreated fabric had extensive bacterial undergrowth.

The results show that the presence of acetic acid in the treating bath prevents precipitation of the insoluble zirconium acetate-sodium perborate complex such as occurred in Example 7, and this permits the treating solution to be applied to cellulosic textiles.

EXAMPLE 10

Preparation of a Water-Insoluble Complex of Zirconyl Acetate with Potassium Peroxydiphosphate To a soluton of 0.69 parts by weight of potassium peroxydiphosphate ($K_4P_2O_8$) in 10 parts water at 23° C. was added 2.3 parts of 40% aqueous zirconyl acetate with stirring. A gelatinous precipitate quickly formed. The solid was filtered by suction, was washed with 50 ml of distilled water, and again filtered. The solid was dried to constant weight under partial vacuum at 3 mm pressure for 3 hours at 23° C., the vacuum being released every hour to permit trituration of the solid to a more finely divided powder. The yield of white solid was 0.16 part by weight. The product had a peroxide content of 2.80% as determined by iodometric titration. The zirconium content was 29.7% and the phosphorus content was 5.13%, with 5.48% acetyl.

EXAMPLE 11

Two-Bath Textile Finishing Process with Zirconyl Acetate and Potassium Peroxydiphosphate Desized, scoured and bleached 80×80 cotton printcloth was immersed in a solution of 4.1% aqueous zirconyl acetate for 1 minute, and then was passed between squeeze rolls adjusted to give a wet pickup of 126%. The cloth was subsequently dried for 5 minutes at 80° C. The fabric was then immersed in a solution of 8% aqueous potassium peroxydiphosphate, was passed between squeeze rolls, was again immersed in the 8% aqueous potassium peroxydiphosphate solution to obtain thorough wetting, and was again passed between squeeze rolls adjusted to give an overall wet pickup of 128% based on original weight of untreated fabric. The cloth was subsequently cured for 5 minutes at 80° C., and was then washed 15 minutes in hot running water. The cloth was dried for 5 minutes at 80° C. After air-equilibration at ordinary humidity, the cloth had a weight gain of 6.3%. The treated cloth was shown by chemical analysis to contain 0.59% zirconium, 0.63% phosphorus, and 0.10% peroxide groups. The cloth showed no bacterial undergrowth when subjected to the parallel streak test with *Staph. aureus* and *K. pneumoniae*. In the Quinn test with *Staph. epidermidis*, the treated fabric had 43% fewer bacterial colonies than did the untreated fabric.

The results show that the potassium peroxydiphosphate underwent complexation with zirconyl acetate already deposited on the fabric as a polymeric zirconium oxyacetate, and the peroxydiphosphate anions were bound to the fabric, thereupon imparting to the fabric a high degree of activity in inhibiting *Staph. aureus* and *K. pneumoniae* bacteria, and a moderate degree of activity in inhibiting *Staph. epidermidis*.

We claim:

1. A process for the preparation of water-insoluble bacteriostatic complexes of zirconyl acetate with hydrogen peroxide, which process comprises:
   (a) mixing an aqueous solution containing about from 10% to 30% hydrogen peroxide with a second aqueous solution containing about from 1% to 40% zirconyl acetate, at a mole ratio of about from 0.1 to 3.0 moles of zirconyl acetate per mole of hydrogen peroxide and a temperature of about from 10° C. to 50° C., to cause water-insoluble complexes to precipitate,
   (b) filtering the insoluble complexes free of any excess liquid,
   (c) washing the insoluble complexes with water to remove excess reagents,
   (d) filtering the insoluble complexes, and
   (e) drying the insoluble complexes.

2. As bacteriostatic complexes, the water-insoluble zirconyl acetate-hydrogen peroxide complexes prouced by the process of claim 1 and characterized by the presence of zirconium, acetyl groups and peroxide groups in the complexes.

3. A process for the preparation of water-insoluble bacteriostatic complexes of zirconyl acetate with alkali metal perborates, which process comprises:
   (a) mixing an aqueous solution containing about from 1% to 10% of an alkali metal perborate selected from the class consisting of an alkali metal perborate monohydrate and an alkali metal perborate tetrahydrate with an aqueous solution containing about from 1% to 40% zirconyl acetate, at a mole ratio of about from 0.1 to 3.0 moles of zirconyl acetate per mole of alkali metal perborate and a temperature of about from 10° C. to 50° C., to cause the insoluble complexes to precipitate,
   (b) filtering the insoluble complexes free of excess liquid,
   (c) washing the insoluble complexes with water to remove excess reagents,
   (d) filtering the insoluble complexes, and
   (e) drying the insoluble complexes.

4. The process of claim 3 where the alkali metal perborate is sodium perborate tetrahydrate.

5. As bacteriostatic complexes, the water-insoluble zirconyl acetate-alkali metal perborate complexes produced by the process of claim 3 and characterized by the presence of acetyl, zirconium, boron, and peroxide groups in the complexes.

6. The complexes of claim 5 where the alkali metal perborate is sodium perborate tetrahydrate.

7. A process for the preparation of water-insoluble bacteriostatic complexes of zirconyl acetate with an alkali metal peroxydiphosphate, which process comprises:
   (a) mixing an aqueous solution containing about from 1% to 10% of the alkali metal peroxydiphosphate with a second aqueous solution containing about from 1% to 40% zirconyl acetate, at a mole ratio of about from 0.1 to 3.0 moles of zirconyl acetate per mole of alkali metal peroxydiphosphate and a temperature of about from 10° C. to 50° C., to cause water-insoluble complexes to precipitate,
   (b) filtering the insoluble complexes free of excess liquid,
   (c) washing the insoluble complexes with water to remove excess reagents,
   (d) filtering the insoluble complexes, and
   (e) drying the insoluble complexes.

8. The process of claim 7 where the alkali metal peroxydiphosphate is potassium peroxydiphosphate.

9. As bacteriostatic complexes, the water-insoluble zirconyl acetate-alkali metal peroxydiphosphate complexes produced by the process of claim 7, and characterized by the presence of zirconium, phosphorus acetyl and peroxide groups in the complexes.

10. The complexes of claim 9 where the alkali metal peroxydiphosphate is potassium peroxydiphosphate.

* * * * *